United States Patent
Bhutada et al.

(10) Patent No.: US 8,614,210 B2
(45) Date of Patent: Dec. 24, 2013

(54) PROCESS FOR PREPARING PHARMACEUTICAL OPHTHALMIC COMPOSITIONS

(75) Inventors: Pravin Meghrajji Bhutada, Pune (IN); Ashish Ashokrao Deshmukh, Pune (IN); Sajeev Chandran, Pune (IN); Shirishkumar Kulkarni, Pune (IN)

(73) Assignee: Lupin Limited, Mumbai, Maharashtra (IN)

( * ) Notice: Subject to any disclaimer, the term of this patent is extended or adjusted under 35 U.S.C. 154(b) by 0 days.

(21) Appl. No.: 13/513,335

(22) PCT Filed: Dec. 2, 2010

(86) PCT No.: PCT/IN2010/000784
§ 371 (c)(1),
(2), (4) Date: Jun. 1, 2012

(87) PCT Pub. No.: WO2011/067791
PCT Pub. Date: Jun. 9, 2011

(65) Prior Publication Data
US 2012/0283252 A1      Nov. 8, 2012

(30) Foreign Application Priority Data
Dec. 3, 2009   (IN) .......................... 1415/KOL/2009

(51) Int. Cl.
*A61P 27/02* (2006.01)
*A61K 31/542* (2006.01)

(52) U.S. Cl.
USPC ...................................... 514/226.5

(58) Field of Classification Search
USPC ....................................................... 514/226.5
See application file for complete search history.

(56) References Cited

U.S. PATENT DOCUMENTS

| 6,071,904 A * | 6/2000 | Ali et al. ..................... 514/222.8 |
| 6,258,350 B1 * | 7/2001 | Mallick ....................... 424/78.04 |
| 2007/0077303 A1 * | 4/2007 | Alli et al. ....................... 424/486 |
| 2009/0048188 A1 * | 2/2009 | Matsuo et al. .................. 514/35 |

OTHER PUBLICATIONS

International Search Report for corresponding International Patent Application No. PCT/IN2010/000784 mailed Dec. 2, 2010.

* cited by examiner

*Primary Examiner* — Jeffrey S. Lundgren
*Assistant Examiner* — Zenab Olabowale
(74) *Attorney, Agent, or Firm* — Merchant & Gould P.C.

(57) ABSTRACT

Pharmaceutical ophthalmic compositions comprising active ingredient(s) such as carbonic anhydrase inhibitor (CAI) or combinations and processes for making such compositions and the use of these compositions in patient populations including pediatric populations. A process for preparing an ophthalmic composition comprising a carbonic anhydrase inhibitor, which comprises a) preparing a slurry comprising a carbonic anhydrase inhibitor and a surfactant; b) preparing a polymer slurry comprising a polymer and water; c) preparing a solution comprising tonicity and preservative agents; d) mixing the polymer slurry of step b and the solution of step c, to form a vehicle concentrate and adjusting pH; e) adding the slurry of step a, to the vehicle concentrate of step d and mixing to homogenize; f) autoclaving the mixture of step e; g) sizing the mixture of step f, under aseptic condition.

9 Claims, 4 Drawing Sheets

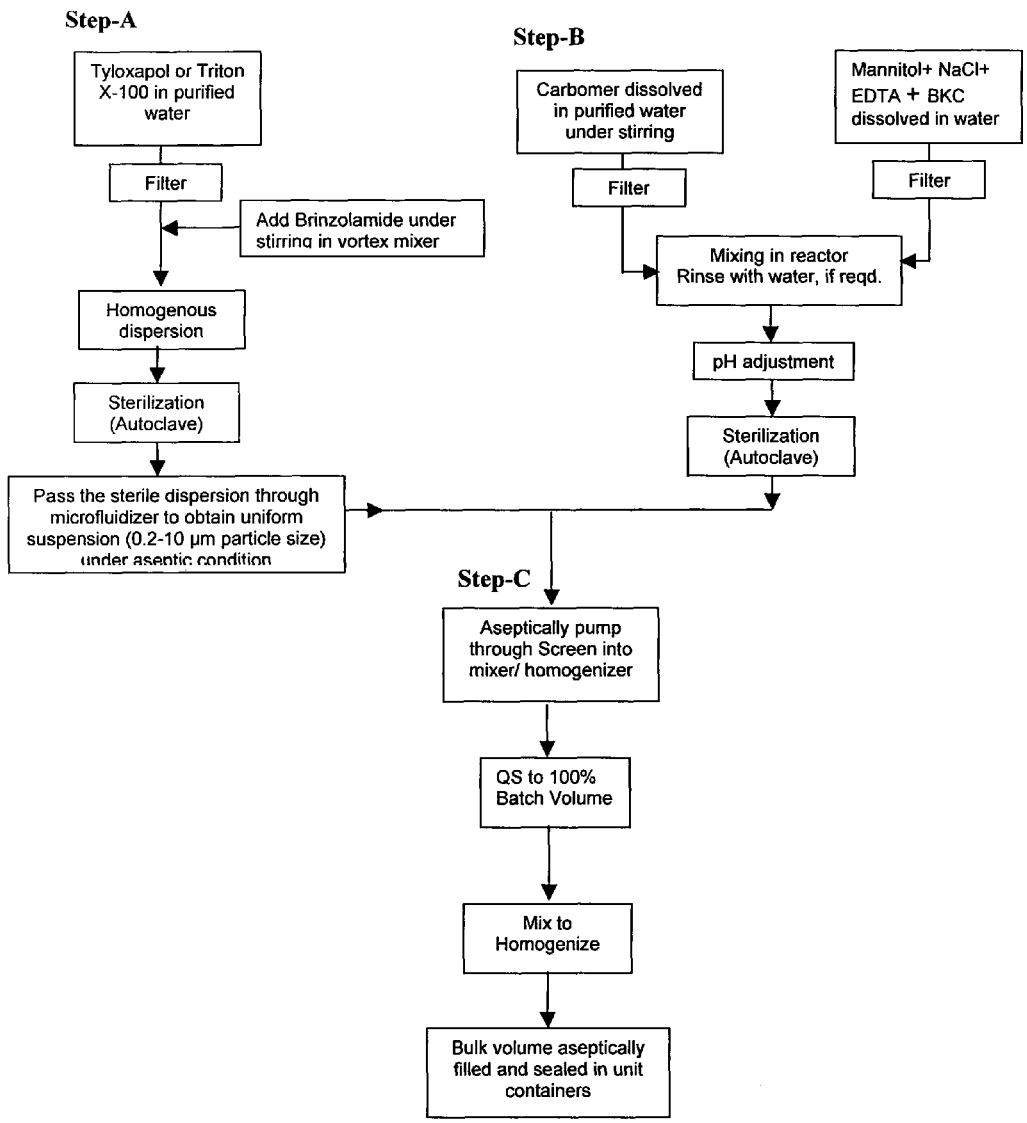
FIGURE- I

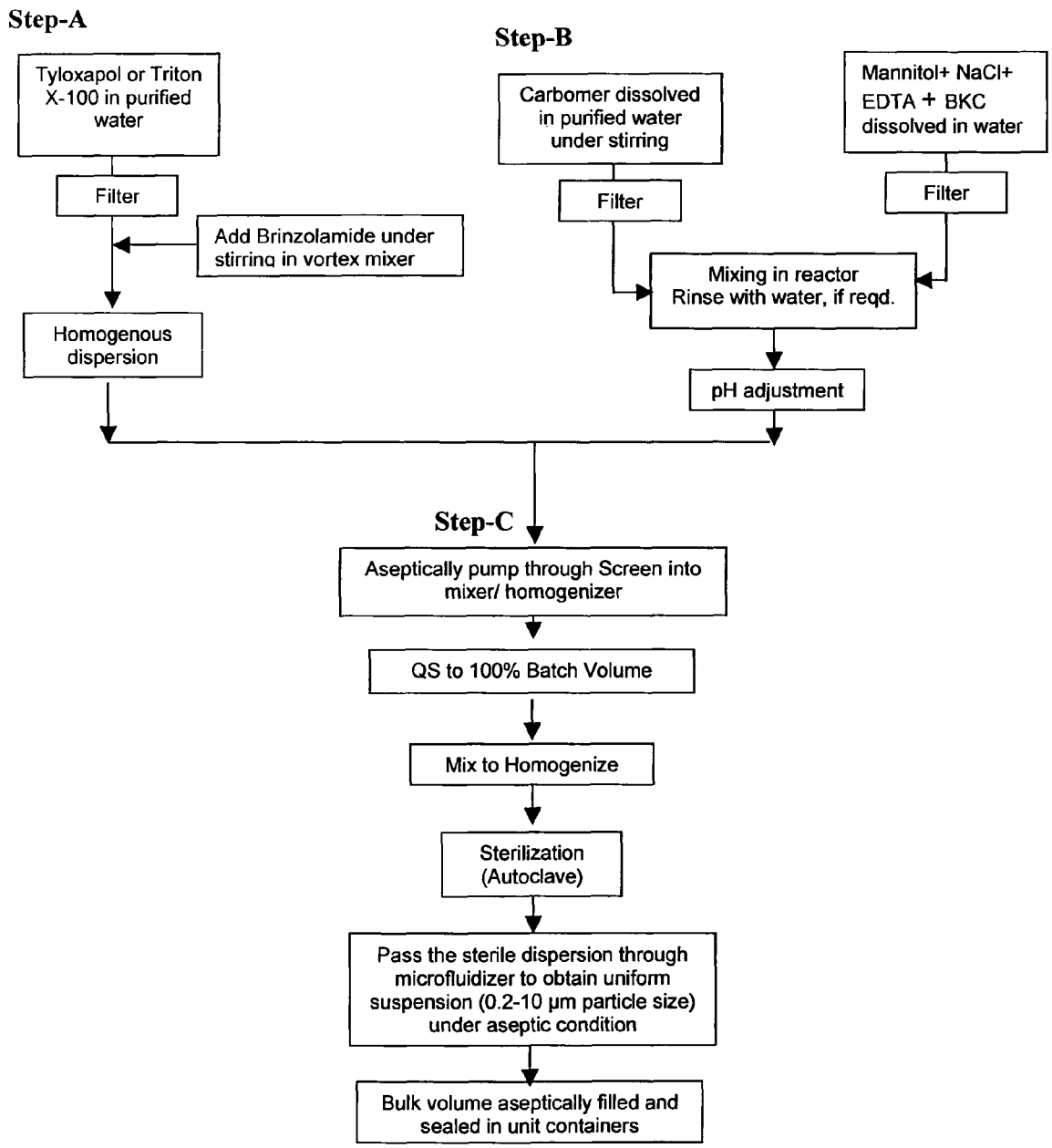
FIGURE-II

Step-A

```
┌──────────────────┐
│ Tyloxapol or Triton│
│ X-100 in purified │
│      water       │
└────────┬─────────┘
         ▼
    ┌────────┐      ┌──────────────────────┐
    │ Filter │◄─────│ Add Brinzolamide under│
    └────┬───┘      │ stirring in vortex mixer│
         │          └──────────────────────┘
         ▼
┌──────────────────┐
│   Homogenous     │
│    dispersion    │
└────────┬─────────┘
```

Step-B

```
┌──────────────────┐         ┌──────────────────┐
│ Carbomer dissolved│         │ Mannitol+ NaCl+  │
│ in purified water │         │ EDTA + BKC       │
│ under stirring    │         │ dissolved in water│
└────────┬─────────┘         └────────┬─────────┘
         ▼                            ▼
    ┌────────┐                   ┌────────┐
    │ Filter │                   │ Filter │
    └────┬───┘                   └────┬───┘
         ▼                            ▼
      ┌─────────────────────────────────┐
      │   Mixing in reactor             │
      │   Rinse with water, if reqd.    │
      └────────────┬────────────────────┘
                   ▼
            ┌──────────────┐
            │ pH adjustment│
            └──────┬───────┘
```

Step-C

```
┌─────────────────────────────────────┐
│ Aseptically pump through Screen into│
│       mixer/ homogenizer            │
└──────────────┬──────────────────────┘
               ▼
┌─────────────────────────────────────┐
│ Sterilize the dispersion along with │
│       milling beads (Autoclave)     │
└──────────────┬──────────────────────┘
               ▼
┌─────────────────────────────────────┐
│ Mill the dispersion in ball mill to │
│ obtain uniform suspension (0.2-10 µm│
│ particle size) under aseptic condition│
└──────────────┬──────────────────────┘
               ▼
┌─────────────────────────────┐
│  QS to 100% Batch Volume    │
└──────────────┬──────────────┘
               ▼
┌─────────────────────────────┐
│      Mix to Homogenize      │
└──────────────┬──────────────┘
               ▼
┌─────────────────────────────────────┐
│ Pass the sized dispersion through   │
│         suitable screen             │
└──────────────┬──────────────────────┘
               ▼
┌─────────────────────────────────────┐
│ Bulk volume aseptically filled and  │
│      sealed in unit containers      │
└─────────────────────────────────────┘
```

FIGURE- III

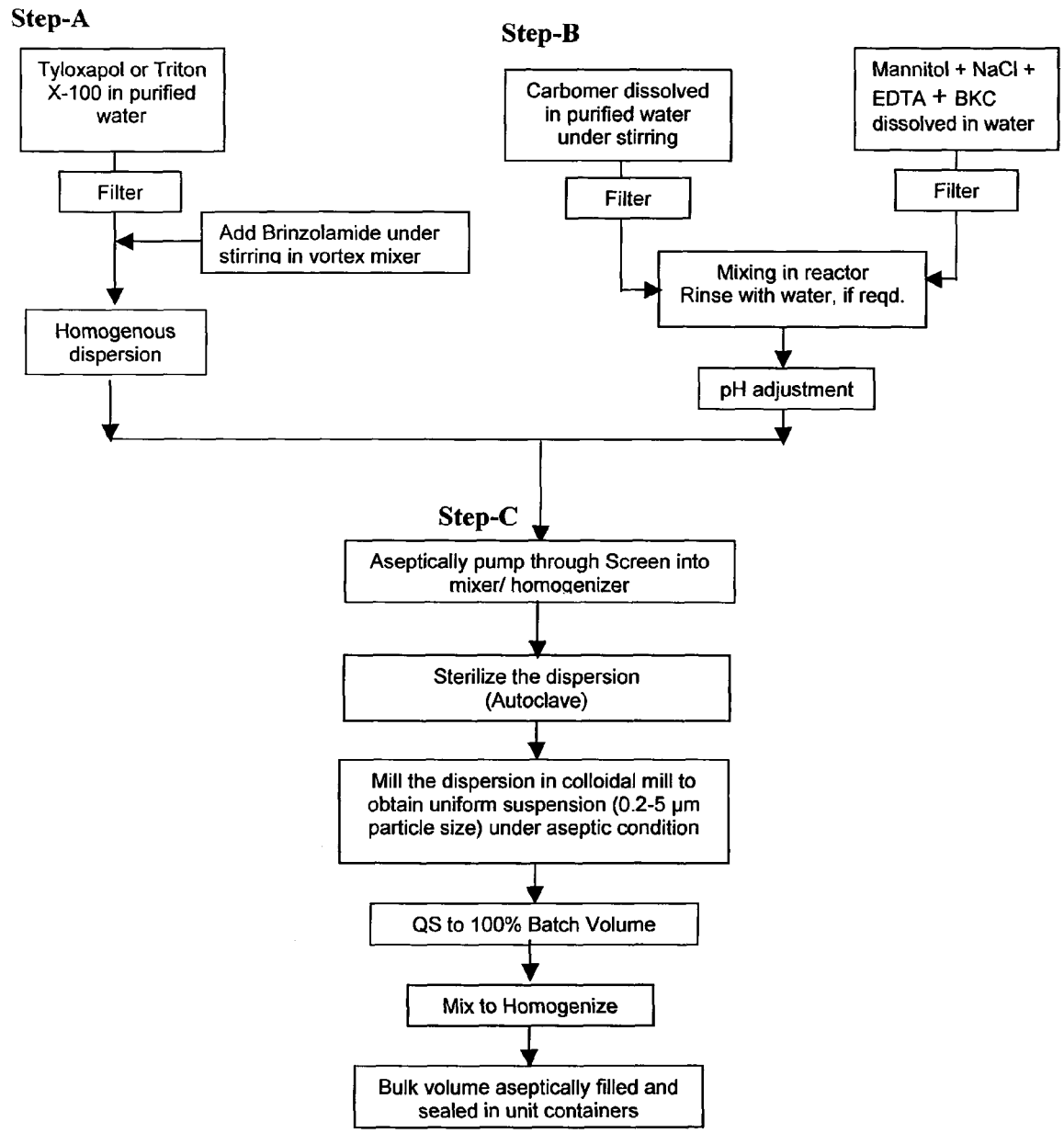
FIGURE- IV

PROCESS FOR PREPARING PHARMACEUTICAL OPHTHALMIC COMPOSITIONS

This application is a National Stage Application of PCT/IN2010/000784, filed 2 Dec. 2010, which claims benefit of Serial No. 1415/KOL/2009, filed 3 Dec. 2009 in India and which applications are incorporated herein by reference. To the extent appropriate, a claim of priority is made to each of the above disclosed applications.

FIELD OF THE INVENTION

This invention relates to pharmaceutical ophthalmic compositions comprising active ingredient(s) such as carbonic anhydrase inhibitor (CAI) or combinations and processes for making such compositions and the use of these compositions in patient populations including pediatric populations.

BACKGROUND OF THE INVENTION

Many useful ophthalmic compounds are solids. Those solids which are soluble in ophthalmic carriers or vehicles present little or no difficulty when preparing a composition for ophthalmic use. However, those solids which are insoluble in ophthalmic carriers must be formulated as compositions such as suspensions or emulsion in order to obtain a proper delivery system. Moreover, forms of useful ophthalmic compounds which are insoluble in ophthalmic carriers are often found desirable in order to prolong the particular therapeutic action of the compound.

A pharmaceutically acceptable ophthalmic composition possesses certain essential characteristics, among which are: (1) the dispersed or suspended material should not settle too rapidly from the carrier to be available in the required concentration in the carrier for effective administration to the eye of the patient; (2) the particles of dispersed or suspended material which do finally settle to the bottom of the vessel holding the composition must not form an intractable hard cake but should be readily re-dispersed into a uniform composition when the vessel is shaken; (3) the particles size of the dispersed materials should be fine enough to avoid any irritation to the eye.

Major problems related to ophthalmic compositions are crystallization and agglomeration of active ingredients during preparation as well as during storage. Crystallization or agglomeration of active leads to non-uniformity of dose, difficulty of administration, irritation to eye due to large drug particles and/or any ocular adverse effect due to high drug concentration or failure of treatment due to low drug concentration.

In most cases crystallization of active ingredients useful for ophthalmic use like carbonic anhydrase inhibitor, beta-blockers or others actives, occurs during preparation. Sterilization by autoclaving leads to increase in solubility of the actives in the preparation and large crystals are formed during cool down phase. Aseptic ball milling of this final composition is not always practical. Aseptic addition of the all actives to a sterile vehicle is also not practical as the all actives cannot be sterilized by conventional means due to stability problem. Dry heat sterilization causes melting of the material. Sterilization by ethylene oxide introduces unacceptable degradation products and residues, and sterilization by gamma irradiation of micronized material produces degradation products unacceptable for regulatory filing. Another reason for crystallization is change in pH due to addition of salts, acids or bases.

During storage, the composition is left standing for a long time, hence secondary particles are formed due to partial agglomeration caused by mutual adhesion of suspended particles, or a hard deposit layer (caking) on the bottom surface of a container; or may have a lowered pH. Such formation of secondary particles or caking causes problems in terms of particle size and re-dispersibility (hereinafter secondary particles and caking are sometimes integrally referred to as agglomerates). It has been found that the caking is common problem due to unequal particle size distribution. The fine particles take the void space in-between the large particles and form strong caking.

In one preferred embodiment, the pharmaceutical ophthalmic compositions comprise pharmaceutically active carbonic anhydrase inhibitors (CAIs) such as R 4-ethylamino-3,4-dihydro-2-(3-methoxy)propyl-2H-thieno[3,2-e]-1,2-thiazine-6-sulfonamide 1,1 dioxide, which is known as brinzolamide. This compound is disclosed in U.S. Pat. No. 5,378,703 (Dean, et al.).

U.S. Pat. No. 6,071,904 discloses processes for preparation of brinzolamide ophthalmic composition.

We have now developed simpler and cost effective process(s) to prepare pharmaceutical ophthalmic compositions.

BRIEF DESCRIPTION OF THE DRAWING

FIG. I is a flow diagram showing the process for making pharmaceutical ophthalmic composition of active ingredient(s) such as carbonic anhydrase inhibitor (e.g. brinzolamide) by two stage autoclaving and sizing of drug concentrate using microfludizer under aseptic condition.

FIG. II is a flow diagram showing the process for pharmaceutical ophthalmic composition of active ingredient(s) such as carbonic anhydrase inhibitor (e.g. brinzolamide) by single stage autoclaving and sizing using microfludizer under aseptic condition.

FIG. III is a flow diagram showing the process for making pharmaceutical ophthalmic composition of active ingredient(s) such as carbonic anhydrase inhibitor (e.g. brinzolamide) by single stage autoclaving and sizing using ball mill under aseptic condition.

FIG. IV is a flow diagram showing the process for making pharmaceutical ophthalmic composition of active ingredient(s) such as carbonic anhydrase inhibitor (e.g. brinzolamide) by single stage autoclaving and sizing using colloidal mill/homogenizer under aseptic condition.

SUMMARY OF THE INVENTION

One of the embodiments relates to pharmaceutical ophthalmic composition comprising active ingredient(s) such as carbonic anhydrase inhibitor (CAI) or combinations and processes for making such compositions and the use of these compositions in patient populations including pediatric populations.

Another embodiment relates to a process for preparing a ophthalmic composition comprising the steps of autoclaving a homogenously dispersed slurry comprising active ingredient(s) such as carbonic anhydrase inhibitor and surfactant(s); sizing the particles of active ingredient(s) of the homogenously dispersed slurry of a by microfludizer; preparing a polymer slurry comprising polymer and water; preparing a solution comprising tonicity and preservative agents; mixing the polymer slurry and the solution to form a vehicle concentrate and adjusting pH; autoclaving the vehicle concentrate; and aseptically adding the sized active ingredient(s) slurry through a screen to the sterilized vehicle concentrate.

Another embodiment relates to a process for preparing a ophthalmic composition comprising the steps of preparing a homogenously dispersed slurry comprising active ingredient(s) such as carbonic anhydrase inhibitor and surfactant(s); preparing a polymer slurry comprising polymer and water; preparing a solution comprising tonicity and preservative agents; mixing the polymer slurry and the solution to form a vehicle concentrate and adjusting pH; aseptically adding the homogenously dispersed active ingredient(s) slurry through a screen to the sterilized vehicle concentrate and mixing to homogenize; autoclaving the active ingredient(s) slurry and vehicle concentrate mixture; and finally, sizing the particles of active ingredient(s) such as carbonic anhydrase inhibitor of the autoclaved mixture by microfludizer under aseptical condition.

DETAILED DESCRIPTION OF THE INVENTION

This invention relates to pharmaceutical ophthalmic compositions comprising active ingredient(s) such as carbonic anhydrase inhibitor (CAI) or combinations thereof and processes for making such compositions.

The term "composition" means a liquid or semi-liquid having solid particles homogeneously dissolved or dispersed in pharmaceutically acceptable solvent or carrier system with or without additional ophthalmic excipient(s). It includes suspension, emulsions, drops, solutions and the like.

The active ingredient is defined as the chemical substance, which is used in the prevention or treatment of various diseases associated with human or non-human animals. The preferred active ingredient includes but are not limited to the active which is useful in the treatment or prevention of diseases associated to eye like elevated intraocular pressure in patients with ocular hypertension or open-angle glaucoma, ocular surface pain, uveitis, scleritis, episcleritis, keratitis, surgically-induced inflammation, endophthalmitis, iritis, atrophic macular degeneration, retinitis pigmentosa, iatrogenic retinopathy, retinal tears and holes, cystoid macular edema, diabetic macular edema, diabetic retinopathy, sickle cell retinopathy, retinal vein and artery occlusion, optic neuropathy, exudative macular degeneration, neovascular glaucoma, corneal neovascularization, cyclitis, sickle cell retinopathy, pterygium, seasonal allergic conjunctivitis, palpebral and bulbar conjunctiva, acne rosacea, superficial punctuate keratitis, herpes zoster keratitis, iritis, cyclitis, selected infective conjunctivitides, post-operative inflammation following ocular surgery.

The active ingredient used in the pharmaceutical ophthalmic composition, may be a soluble or sparingly soluble or slightly soluble or very slightly soluble or practically insoluble compound(s) selected from the group but are not limited to a carbonic anhydrase inhibitor (CAI), such as brinzolamide, acetazolamide, dorzolamide, methazolamide; a beta-blocker, such as timolol, arteolol, metopranolol, betaxolol; non steroidal anti-inflammatory drugs (NSAID), such as nepafenac, flurbiprofen, diclofenac and ketorolac tromethamine; an antifungal agent, such as natamycin, amphotericin-B; an α-2 adrenergic agonist, such as epinephrine, dipivefrin, brimonidine, apraclonidine; a prostaglandin analog, such as latanoprost, travoprost, bimatoprost; a phosphodiesterase IV inhibitor (PDE-IV or PDE-4) inhibitor, such as roflumilast; a receptor tyrosine kinase inhibitor; a steroid, such as fluorometholone, hydrocortisone, dexamethasone, prednisolone, loteprednol, or medrysone; an antibiotic; an antibacterial agent[0]s or other actives used for ophthalmic formulation or a pharmaceutically acceptable salt(s), hydrate(s), solvate(s), polymorph(s), stereoisomer(s), ester(s), prodrug(s), complex(es) and their metabolites thereof. All of the foregoing actives are known compounds and can be made by known methods and can be used in various combinations. One of the preferred active is a CAI, or a beta-blocker or a steroid. In a preferred embodiment the CAI is brinzolamide, can be in combination with a beta-blocker.

The term active ingredient(s) can be interchangeably used with their pharmaceutically acceptable salt(s), hydrate(s), solvate(s), polymorph(s), stereoisomer(s), ester(s), prodrug(s), complex(es) and their metabolites thereof.

The pharmaceutical ophthalmic composition comprises a pharmaceutically acceptable solvent or carrier system and an active ingredient dispersed in said solvent or carrier system. The pharmaceutically acceptable solvent may be, for example, an aqueous solvent such as water, physiological saline and buffer. While the active ingredient content may vary depending on type of active, diseases to be treated and the like, it is generally present in a proportion of 0.005-20.0 w/v %, preferably 0.005-5.0 w/v % relative to the entire composition. The pharmaceutically acceptable solvent or carrier system is defined as the media in which the active is dispersed and may be aqueous or buffer system or likewise. The solvent or carrier system may contain various additives such as a viscosity agent, a stabilizer, a preservative, a surfactant, an antioxidant, a chelating agent, a pH adjusting agent, a thickener and an absorption promoter which are known to a skilled person in art.

The viscosity agents used in the pharmaceutical ophthalmic composition may comprise a water soluble polymer for enhancing dispersion stability. Examples of the water soluble polymer include but not limited to polymers like polyacrylic acids (e.g. carbomer), hydroxypropyl-methylcellulose, polyvinyl alcohol, hydroxyethylcellulose, hydroxypropylcellulo se, polyvinylpyrrolidone, polyethylene glycol, sodium carboxymethylcellulose, methylcellulose, ethylcellulose, sodium alginate, gelatin, carboxyvinyl polymer and mixtures thereof. Other suspending agents known in the field of pharmaceutical preparation may be also contained. Of the above-mentioned water soluble polymers, polymer like carbomer, hydroxypropylmethylcellulose and polyvinyl alcohol are preferable, since they suppress formation of agglomerates, prevent lowering of pH, and provide a composition superior in redispersibility and stability. The water soluble polymer is generally present in a composition in a proportion of 0.01-2.0 w/v %, preferably 0.02-1.0 w/v %, more preferably 0.03-0.8 w/v % relative to the entire composition.

The surfactants used in the pharmaceutical ophthalmic composition for enhancing dispersion stability preferably include nonionic surfactant(s). The nonionic surfactant to be used is non-toxic, non-irritant and applicable to the eye. Non-limiting examples of the nonionic surfactant include polymer of the alkyl aryl polyether alcohol like tyloxapol; polyoxyethylene polyoxypropylene polymer like triton X-100; polyoxyethylenesorbitan fatty acid esters such as polyoxyethylenesorbitan monooleate, polyoxyethylenesorbitan monolaurate, polyoxyethylenesorbitan monopalmitate and polyoxyethylenesorbitan monostearate; polyoxyethylene hydrogenated castor oils; sorbitan fatty acid esters such as sorbitan monooleate, sorbitan monolaurate, sorbitan monopalmitate and sorbitan monostearate; polyoxyethylene alkyl ethers such as polyoxyethylene lauryl ether; and polyoxyethylene fatty acid esters such as polyoxyethylene monostearate and mixtures thereof. Of the recited nonionic surfactants, alkyl aryl polyether alcohol like tyloxapol, polyoxyethylene polyoxypropylene polymer like triton X-100 are preferable, since they suppress formation of agglomerates, prevent lowering of pH, and provide a composition superior in redispersibility and stability. The nonionic surfactant is generally contained in a proportion of 0.005-1.0 w/v %, preferably 0.01-0.5 w/v % and more preferably 0.05-0.3 w/v % relative to the entire composition.

The pharmaceutical ophthalmic composition optionally comprises preservative(s) for preventing contamination with microorganisms such as fungi and bacteria. The preservative usable has antibacterial action and antifungal action, and should be non-toxic, non-irritant and applicable to the eye. Examples of the preservative include quaternary ammonium salts such as benzalkonium chloride and benzethonium chloride; cationic compounds such as chlorhexidine gluconate; p-hydroxybenzoates such as methyl p-hydroxybenzoate, ethyl p-hydroxybenzoate, propyl p-hydroxybenzoate and butyl p-hydroxybenzoate; alcohol compounds such as chlorobutanol and benzyl alcohol; sodium dehydroacetate; and thiomersal and mixtures thereof. Of the recited preservatives, quaternary ammonium salts and cationic compounds are preferable as they suppress formation of agglomerates, prevent lowering of pH, and provide a composition superior in redispersibility and stability. Of the quaternary ammonium salts, benzalkonium chloride and benzethonium chloride are particularly preferable, and chlorhexidine gluconate is particularly preferable as the cationic compound. The preservative is generally contained in a proportion of 0.001-0.3 w/v %, preferably 0.002-0.05 w/v % and more preferably 0.005-0.01 w/v % relative to the entire composition.

Non-limiting examples of tonicity agents include sodium chloride, glycerol, glucose, mannitol and sorbitol, which are conventionally used for eye drops. Of these, sodium chloride is preferable as it possesses superior dispersibility when formulated into a preparation, suppresses formation of agglomerates and provides a composition superior in redispersibility. The tonizing agent is added in such an amount that makes the osmotic pressure of the composition identical to that of tears.

The pharmaceutical ophthalmic composition may further include a buffer. The buffer should have buffering capacity in the range of pH 5.0-8.5. Examples of the buffer include acetates such as sodium acetate; phosphates such as sodium dihydrogenphosphate, disodium hydrogenphosphate, potassium dihydrogenphosphate and dipotassium hydrogenphosphate; $\epsilon$-aminocaproic acid; amino acid salts such as sodium glutamate; and boric acid and a salt thereof. Of the mentioned buffers, acetates and $\epsilon$-aminocaproic acid are preferable as they suppress formation of agglomerates, prevent lowering of pH, and provide a composition superior in redispersibility and stability. As the acetate, sodium acetate is particularly preferable. The buffer is generally contained in a proportion of 0.01-2.0 w/v %, preferably 0.05-0.5 w/v % relative to the entire composition.

Examples of the pH adjusting agent include hydrochloric acid, citric acid, phosphoric acid, acetic acid, tartaric acid, sodium hydroxide, potassium hydroxide, sodium carbonate and sodium hydrogencarbonate. The pharmaceutical ophthalmic composition is generally adjusted to pH 4-10, the range which is less irritating to the mucosal membrane of the eye.

Suitable chelating agents include edetate disodium, edetate trisodium, edetate tetrasodium, diethyleneamine pentaacetate and mixtures thereof. Most preferred is edetate disodium. The chelating agent is generally present in an amount from 0.001-0.1 w/v % relative to the entire composition. In the case of edetate disodium, the chelating agent is preferably present at a concentration of 0.005-0.05 w/v % relative to the entire composition.

Examples of the antioxidant include ascorbic acid, sodium ascorbate, tocopherol and sulfite salts like sodium sulfite, potassium sulfite, magnesium sulfite, calcium sulfite, sodium bisulfite, potassium bisulfite, magnesium bisulfite, calcium bisulfite, sodium metabisulfite, potassium metabisulfite, calcium metabisulfite, sodium thiosulfate and sodium hydrogensulfite. The sulfite salt is generally be present in an amount from 0.01-1% w/v % relative to the entire composition.

The average particle size of the dispersed or the suspended active is generally 0.01-100 µm. The more acceptable particle size range is 0.01-50 µm, preferably 0.01-30 µm, more preferably 0.1-20 µm and most preferably 0.1-5.0 µm. The use of the active in this particle size range affords a composition having superior dispersibility, which is less irritating to the mucosal membrane of the eye.

In one embodiment, microfluidization technique is used for sizing of particles in the preparation of pharmaceutical ophthalmic composition. There are various advantages of Microfluidizer Processor Technology which include much smaller particle and droplet size; much more uniform particle and droplet size distribution; faster processing times (>2 orders of magnitude in some applications); better control of the amount of energy applied; much higher energy (up to 40,000 psi sustained); scalability from small batches to continuous production; no moving parts in the interaction chamber; easy to clean in many applications; little or no contamination; uniform and dispersions and emulsions; highly repeatable process from run to run or batch to batch. Additional advantages are lower processing cost, increased speed of operation and more flexible manufacturing capability in the face of evolving market opportunities.

One of the embodiments relates to various processes to prepare pharmaceutical ophthalmic composition.

In one embodiment the process to prepare a pharmaceutical ophthalmic composition comprises one or two stage sterilization by autoclaving and use of microfluidization technique for sizing of particles.

In another embodiment the process to prepare a pharmaceutical ophthalmic composition comprises one stage sterilization by autoclaving and use of ball mill for sizing of particles.

In another embodiment the process to prepare a pharmaceutical ophthalmic composition comprises one stage sterilization by autoclaving and use of colloidal mill or homogenizer for sizing of particles.

In another embodiment the process to prepare a pharmaceutical ophthalmic composition comprises use of microfluidization technique for sizing of particles of active ingredient(s) such as carbonic anhydrase inhibitor (e.g. brinzolamide).

In another embodiment the process to prepare a pharmaceutical ophthalmic composition comprises one or two stage sterilization by autoclaving and use of microfluidization technique for sizing of particles of active ingredient(s) such as carbonic anhydrase inhibitor (e.g. brinzolamide).

In another embodiment the process to prepare a pharmaceutical ophthalmic composition comprises one stage sterilization by autoclaving and use of ball mill for sizing of particles of active ingredient(s) such as carbonic anhydrase inhibitor (e.g. brinzolamide).

In another embodiment the process to prepare a pharmaceutical ophthalmic composition comprises one stage sterilization by autoclaving and use of colloidal mill or homogenizer for sizing of particles of active ingredient(s) such as carbonic anhydrase inhibitor (e.g. brinzolamide).

Another embodiment processes for preparing pharmaceutical ophthalmic compositions comprising brinzolamide.

The process for making pharmaceutical ophthalmic composition of active ingredient(s) such as carbonic anhydrase inhibitor, more preferably brinzolamide, uses autoclaving of concentrated slurry of brinzolamide and then sizing brinzolamide particles by using microfluidizer and then adding the slurry to the rest of the autoclaved ingredients as shown in FIG. I.

Referring to FIG. I, first the menstruum comprising surfactant(s) such as Tyloxapol or Triton X-100 is prepared by dissolving in purified water and filtering through 2-5 μm filter. The active ingredient(s) such as carbonic anhydrase inhibitor, more preferably brinzolamide (particle size: $d_{(0.9)}$<20 μm and preferably <10 μm) is added to the above menstruum under stirring in vortex mixer to obtain a homogenous dispersion. The above homogenous dispersion is sterilized by autoclaving at normal temperatures and pressures known to those skilled in the art, e.g., 110-129° C., preferably 121-127° C., for 30 min to 3 hour. The particles of sterilized dispersion are sized by passing through a microfluidizer to obtain dispersion with average particle size distribution in the range 0.2-10 μm under aseptic condition.

After sizing, the micronized slurry is aseptically added through a screen to the rest of the ingredients including, water, one or more tonicity agents, one or more preservatives, and at least one polymer which are mixed, filtered, pH adjusted, and sterilized prior to their combination with the milled mixture. The purified water is used to rinse the microfluidizer is then added to the mixture and the batch is brought to final volume aseptically and mixed until homogeneous.

Referring to FIG. II, the process for preparing composition is different from FIG. I. In this process, the active ingredient(s) such as carbonic anhydrase inhibitor, more preferably brinzolamide homogenous dispersion is aseptically added to the rest of the ingredients including, water, one or more tonicity agents, optionally one or more preservatives, and at least one polymer which are mixed, filtered, pH adjusted and then homogenized. The homogenized slurry is made up to the final volume, sterilized by autoclaving and then particle sizing is done by microfluidizer.

Referring to FIGS. III & IV, the process for preparing composition is same as shown in FIG. II but using different types of sizing techniques like ball milling and colloidal milling respectively.

Given below are the examples which merely as illustration of pharmaceutical ophthalmic composition and do not restrict the general concept of the invention.

EXAMPLES

Example 1

| S. No. | Ingredients | Qty (%) |
| --- | --- | --- |
| 1 | Brinzolamide | 1 |
| 2 | Benzalkonium Chloride | 0-0.01 |
| 3 | Mannitol | 0.5-2.4 |
| 4 | Carbopol | 0.05-0.5 |
| 5 | Tyloxapol | 0.03-0.3 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 2

| S. No. | Ingredients | Qty (%) |
| --- | --- | --- |
| 1 | Brinzolamide | 1 |
| 2 | Benzalkonium Chloride | 0-0.01 |
| 3 | Mannitol | 0.5-2.4 |
| 4 | Hypromellose | 0.05-0.5 |
| 5 | Tyloxapol | 0.03-0.3 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 3

| S. No. | Ingredients | Qty (%) |
| --- | --- | --- |
| 1 | Brinzolamide | 1 |
| 2 | Benzalkonium Chloride | 0-0.01 |
| 3 | Mannitol | 0.5-2.4 |
| 4 | Hydroxyethylcellulose | 0.05-0.5 |
| 5 | Polysorbate | 0.05-4.0 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 4

| S. No. | Ingredients | Qty (%) |
| --- | --- | --- |
| 1 | Brinzolamide | 1 |
| 2 | Benzalkonium Chloride | 0-0.01 |
| 3 | Mannitol | 0.5-2.4 |
| 4 | Hydroxy propyl cellulose | 0.05-0.5 |
| 5 | Tyloxapol | 0.03-0.3 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 5

| S. No. | Ingredients | Qty % |
| --- | --- | --- |
| 1 | Brinzolamide | 1 |
| 2 | Benzalkonium Chloride | 0-0.01 |
| 3 | Mannitol | 0.5-2.4 |
| 4 | Hydroxy ethyl cellulose | 0.05-0.5 |
| 5 | Polysorbate | 0.05-4.0 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 6

| S. No. | Ingredients | Qty % |
| --- | --- | --- |
| 1 | Brinzolamide | 1 |
| 2 | Benzalkonium Chloride | 0.01 |
| 3 | Mannitol | 0.5-2.4 |
| 4 | Hydroxypropylcellulose | 0.05-0.5 |
| 5 | Polysorbate | 0.05-4.0 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 7

| S. No. | Ingredients | Qty % |
| --- | --- | --- |
| 1 | Brinzolamide | 1 |
| 2 | Benzalkonium Chloride | 0-0.01 |
| 3 | Mannitol | 0.5-2.4 |
| 4 | Hypromellose | 0.05-0.5 |
| 5 | Polysorbate | 0.05-4.0 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 8

| S. No. | Ingredients | Qty % |
| --- | --- | --- |
| 1 | Brinzolamide | 1 |
| 2 | Benzalkonium Chloride | 0-0.01 |
| 3 | Mannitol | 0.5-2.4 |
| 4 | Methylcellulose | 0.05-0.5 |
| 5 | Tyloxapol | 0.03-0.3 |
| 6 | Edetate Disodium | 0.013-0.13 |
| 7 | Sodium Chloride | 0.085-0.85 |
| 9 | Sodium Hydroxide/ Hydrochloric Acid | q.s. |

Example 9

| S. No. | Ingredients | Qty % |
| --- | --- | --- |
| 1 | Brinzolamide | 1 |
| 2 | Benzalkonium Chloride | 0-0.01 |
| 3 | Mannitol | 0.5-2.4 |
| 4 | Sodium carboxymethylcellulose | 0.05-0.5 |
| 5 | Tyloxapol | 0.03-0.3 |
| 6 | Edetate Disodium | 0.013-0.13 |
| 7 | Sodium Chloride | 0.085-0.85 |
| 9 | Sodium Hydroxide/ Hydrochloric Acid | q.s. |

Brief Manufacturing Procedure

The processes for preparation of pharmaceutical ophthalmic compositions are as set forth.

Method 1: Two Stage Autoclaving and Sizing of Drug Concentrate Using Microfluidizer Step-A: API Slurry Preparation:
1. Dissolve Tyloxapol or Triton X-100 in purified water & filter through 2-5 µm filter.
2. Add Brinzolamide (particle size: $d_{(0.9)}$<20 µm and preferably <10 µm) to solution of step 1 under stirring using a vortex mixer to obtain a homogenous dispersion.
3. Sterilize the dispersion of step 2 by autoclaving.
4. Pass the sterilized dispersion of step 3 through microfluidizer to obtain dispersion with average particle size distribution in the range 0.2-10 µm under aseptic condition.

Step-B: Preparation of Vehicle Concentrate:
5. Add carbomer in sufficient quantity of purified water under continuous stirring in vortex mixer to obtain a uniform dispersion and filter through suitable filter (NMT 10 µm).
6. Dissolve required quantity of mannitol, sodium chloride, benzalkonium chloride & edetate disodium in sufficient quantity of purified water and filter through suitable filter (2-5 µm).
7. Mix solution of step 6 to the dispersion of step 5 under stirring in vortex mixer to obtain vehicle concentrate.
8. Adjust the pH of the dispersion.
9. Sterilize the dispersion of step 8 by autoclaving.

Step-C: Preparation of final composition (In aseptic area):
10. Aseptically pump output of Step A & B into mixer/homogenizer under continuous stirring.
11. Make up the volume to 100% batch size using sterile water rinse.
12. Homogenize the mixture, if required.
13. Bulk volume obtained is aseptically filled and sealed in unit containers.

Method 2: Single Stage Autoclaving and Sizing of the Final Dispersion by Microfluidizer Step-A: API Slurry Preparation:
1. Dissolve Tyloxapol or Triton X-100 in purified water & filter through 2-5 µm filter.
2. Add Brinzolamide (particle size: $d_{(0.9)}$<20 µm and preferably <10 µm) to solution of step 1 under stirring using a vortex mixer to obtain a homogenous dispersion.

Step-B: Preparation of Vehicle Concentrate:
3. Add carbomer in sufficient quantity of purified water under continuous stirring in vortex mixer to obtain a uniform dispersion and filter through suitable filter (NMT 10 µm).
4. Dissolve required quantity of mannitol, sodium chloride, benzalkonium chloride & edetate disodium in sufficient quantity of purified water and filter through suitable filter (2-5 µm).
5. Mix solution of step 4 to the dispersion of step 3 under stirring in vortex mixer to obtain vehicle concentrate.
6. Adjust the pH of the dispersion.

Step-C: Preparation of Final Composition (in Aseptic Area):
7. Mix output of Step A & B in mixer/homogenizer until a uniform dispersion is obtained.
8. Make up the volume to 100% batch size using sterile water rinse.
9. Re-homogenize the dispersion, if required.
10. Sterilize the dispersion of step 9 by autoclaving.
11. Pass the sterilized dispersion of step 10 through microfluidizer to obtain dispersion with average particle size distribution in the range 0.2-10 µm under aseptic condition.
12. Bulk volume obtained is aseptically filled and sealed in unit containers.

Method 3: Single Stage Autoclaving and Sizing of the Final Dispersion by Ball Milling
Step-A: API Slurry Preparation:
1. Dissolve Tyloxapol or Triton X-100 in purified water & filter through 2-5 μm filter.
2. Add Brinzolamide (particle size: $d_{(0.9)}$<20 μm and preferably <10 μm) to solution of step 1 under stirring using a vortex mixer to obtain a homogenous dispersion.

Step-B: Preparation of Vehicle Concentrate:
3. Add carbomer in sufficient quantity of purified water under continuous stirring in vortex mixer to obtain a uniform dispersion and filter through suitable filter (NMT 10 μm).
4. Dissolve required quantity of mannitol, sodium chloride, benzalkonium chloride & edetate disodium in sufficient quantity of purified water and filter through suitable filter (2-5 μm).
5. Mix solution of step 4 to the dispersion of step 3 under stirring in vortex mixer to obtain vehicle concentrate.
6. Adjust the pH of the dispersion.

Step-C: Preparation of Final Composition (in Aseptic Area):
7. Mix output of Step A & B in mixer/homogenizer until a uniform dispersion is obtained.
8. Sterilize the dispersion of step 7 along with milling beads by autoclaving in ball mill bottle.
9. Aseptically mill the dispersion of step 10 in ball mill to obtain dispersion with average particle size distribution in the range 0.2-10 μm under aseptic condition.
10. Pass the sized dispersion through suitable screen.
11. Make up the volume to 100% batch size using sterile water rinse.
12. Re-homogenize the dispersion, if required.
13. Bulk volume obtained is aseptically filled and sealed in unit containers.

Method 4: Single Stage Autoclaving and Sizing of the Final Dispersion by Colloidal Mill/Homogenizer
Step-A: API Slurry Preparation:
1. Dissolve Tyloxapol or Triton X-100 in purified water & filter through 2-5 μm filter.
2. Add Brinzolamide (particle size: $d_{(0.9)}$<10 μm and preferably <5 μm) to solution of step 1 under stirring using a vortex mixer to obtain a homogenous dispersion.

Step-B: Preparation of Vehicle Concentrate:
3. Add carbomer in sufficient quantity of purified water under continuous stirring in vortex mixer to obtain a uniform dispersion and filter through suitable filter (NMT 10μ).
4. Dissolve required quantity of mannitol, sodium chloride, benzalkonium chloride & edetate disodium in sufficient quantity of purified water and filter through suitable filter (2-5 μm).
5. Mix solution of step 4 to the dispersion of step 3 under stirring in vortex mixer to obtain vehicle concentrate.
6. Adjust the pH of the dispersion.

Step-C: Preparation of Final Composition (in Aseptic Area):
7. Mix output of Step A & B in mixer/homogenizer until a uniform dispersion is obtained.
8. Sterilize the dispersion of step 7 by autoclaving.
9. Autoclave the required colloidal mill components.
10. Aseptically mill the dispersion of step 10 in colloidal mill to obtain dispersion with average particle size distribution in the range 0.2-5 μm under aseptic condition.
11. Make up the volume to 100% batch size using sterile water rinse.
12. Re-homogenize the dispersion, if required.
13. Bulk volume obtained is aseptically filled and sealed in unit Containers.

The invention claimed is:

1. A process for preparing an ophthalmic composition comprising a carbonic anhydrase inhibitor, which comprises
    a) preparing a slurry comprising a carbonic anhydrase inhibitor and a surfactant;
    b) preparing a polymer slurry comprising a polymer and water;
    c) preparing a solution comprising tonicity and preservative agents;
    d) mixing the polymer slurry of step b and the solution of step c, to form a vehicle concentrate and adjusting pH;
    e) adding the slurry of step a, to the vehicle concentrate of step d and mixing to homogenize;
    f) autoclaving the mixture of step e;
    g) sizing the mixture of step f, under aseptic condition; wherein the process comprises only single stage autoclaving.

2. The process of claim 1 wherein the carbonic anhydrase inhibitor is brinzolamide.

3. The process of claim 1 wherein sizing is carried out by using microfluidizer, ball mill or colloidal mill.

4. The process of claim 1 wherein the polymer is selected from carbomer, hydroxypropylmethylcellulose, polyvinyl alcohol, hydroxyethylcellulose, hydroxypropylcellulose, polyvinylpyrrolidone, polyethylene glycol, sodium carboxymethylcellulose, methylcellulose, ethylcellulose, sodium alginate, gelatin, carboxyvinyl polymer or mixtures thereof.

5. The process of claim 1 wherein the surfactant is selected from alkyl aryl polyether alcohol, polyoxyethylene polyoxypropylene polymer, polyoxyethylenesorbitan fatty acid esters, polyoxyethylene hydrogenated castor oils, sorbitan fatty acid esters, polyoxyethylene alkyl ethers, polyoxyethylene fatty acid esters or mixtures thereof.

6. The process of claim 1 wherein the preservative is selected from benzalkonium chloride, benzethonium chloride, chlorhexidine gluconate, methyl p-hydroxybenzoate, ethyl p-hydroxybenzoate, propyl p-hydroxybenzoate, butyl p-hydroxybenzoate, chlorobutanol, benzyl alcohol, sodium dehydroacetate, thiomersal or mixtures thereof.

7. The process of claim 1 wherein the tonicity agent is selected from sodium chloride, glycerol, glucose, mannitol, sorbitol or mixtures thereof.

8. A process for preparing an ophthalmic composition comprising a carbonic anhydrase inhibitor, which comprises
    a) autoclaving a slurry comprising a carbonic anhydrase inhibitor and a surfactant;
    b) aseptically sizing the particles of the dispersed slurry of step a by microfluidizer;
    c) preparing a polymer slurry comprising a polymer and water;
    d) preparing a solution comprising tonicity and preservative agents;
    e) mixing the polymer slurry of step c and the solution of step d to form a vehicle concentrate and adjusting pH;
    f) autoclaving the vehicle concentrate; and
    g) aseptically adding the slurry of step b to the sterilized vehicle concentrate of step f.

9. The process of claim 8 wherein the carbonic anhydrase inhibitor is brinzolamide.

* * * * *